United States Patent
Perez et al.

(12) 
(10) Patent No.: US 6,171,283 B1
(45) Date of Patent: Jan. 9, 2001

(54) DISPOSABLE SELF-SHIELDING UNIT DOSE SYRINGE GUARD

(75) Inventors: Anthony R Perez, Pasadena, CA (US); John R Firth, Wilsonville, OR (US)

(73) Assignee: Safety Syringes, Inc., Arcadia, CA (US)

(*) Notice: Under 35 U.S.C. 154(b), the term of this patent shall be extended for 0 days.

(21) Appl. No.: 08/814,199

(22) Filed: Mar. 10, 1997

(51) Int. Cl.⁷ ............................... A61M 5/32; A61M 5/00
(52) U.S. Cl. ..................... 604/192; 604/187; 604/181; 604/263
(58) Field of Search ..................... 604/198, 192, 604/232, 187, 181, 234, 263, 218, 110, 111, 197; 128/919

(56) References Cited

U.S. PATENT DOCUMENTS

| | | | |
|---|---|---|---|
| 4,927,416 | 5/1990 | Tomkiel . | |
| 4,969,877 | 11/1990 | Kornberg | 604/195 |
| 5,000,744 | * 3/1991 | Hoffman et al. | 604/232 |
| 5,002,537 | * 3/1991 | Hoffman et al. | 604/232 |
| 5,059,185 | * 10/1991 | Ryan | 604/198 |
| 5,067,945 | * 11/1991 | Ryan et al. | 604/198 |
| 5,098,382 | * 3/1992 | Haber et al. | 604/232 |
| 5,201,720 | * 4/1993 | Borgia et al. | 604/232 |
| 5,215,535 | 6/1993 | Gettig et al. | 604/198 |
| 5,269,766 | * 12/1993 | Haber et al. | 604/232 |
| 5,336,185 | 8/1994 | Lynch et al. . | |
| 5,344,407 | 9/1994 | Ryan | 604/192 |
| 5,385,557 | 1/1995 | Thompson | 604/198 |
| 5,417,660 | 5/1995 | Martin | 604/110 |
| 5,433,712 | * 7/1995 | Stiles et al. | 604/198 |
| 5,437,647 | * 8/1995 | Firth et al. | 604/110 |
| 5,445,620 | 8/1995 | Haber et al. | 604/232 |
| 5,496,286 | * 3/1996 | Stiehl et al. | 604/232 |
| 5,498,244 | 3/1996 | Eck | 604/198 |
| 5,514,107 | 5/1996 | Haber et al. | 604/197 |
| 5,522,812 | * 6/1996 | Talonn et al. | 604/198 |
| 5,569,211 | 10/1996 | Lekhgolts et al. | 604/195 |
| 5,573,512 | 11/1996 | van den Haak | 604/171 |
| 5,624,400 | * 4/1997 | Firth et al. | 604/232 |
| 5,855,839 | * 1/1999 | Brunell | 604/198 |

FOREIGN PATENT DOCUMENTS

| | | |
|---|---|---|
| 0740942 | * 11/1996 | (EP) . |
| 2283425 | * 5/1995 | (GB) . |

* cited by examiner

*Primary Examiner*—Sharon Kennedy
*Assistant Examiner*—Michael J. Hayes
(74) *Attorney, Agent, or Firm*—Lyon & Lyon LLP

(57) ABSTRACT

The present invention is directed to an improved guard for a medical cartridge, such as a unit dose syringe or ampule, comprising a body for receiving the cartridge, and a shield slidably attached to the body. In one form, the guard includes only two parts which are preassembled and ready to receive a cartridge having its own plunger. The body has locking detents which permanently hold the cartridge in the guard, and has cooperating detents and detent pockets which allow the shield to be directed distally, from an unguarded position in which the needle on the cartridge is uncovered for delivery of medication, to a guarded position in which the needle is permanently covered for disposal. In a second form, the guard also includes a plunger assembly for a cartridge not having its own plunger. The plunger assembly is locked onto the body, permanently holding the cartridge received therein. The parts of the device are preferably molded from plastic and may be clear or of a color, such as a latex color or skin tone.

7 Claims, 17 Drawing Sheets

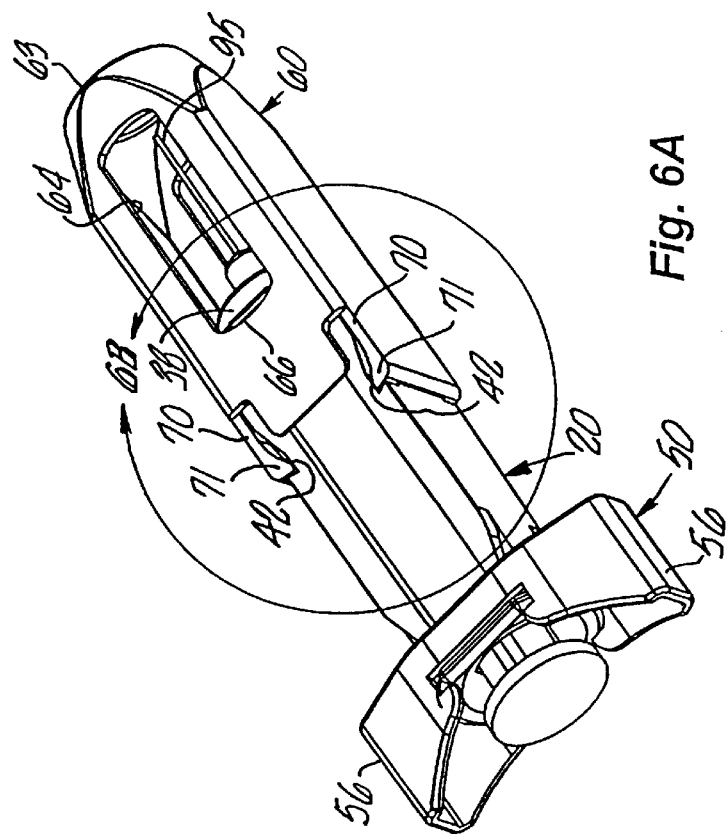
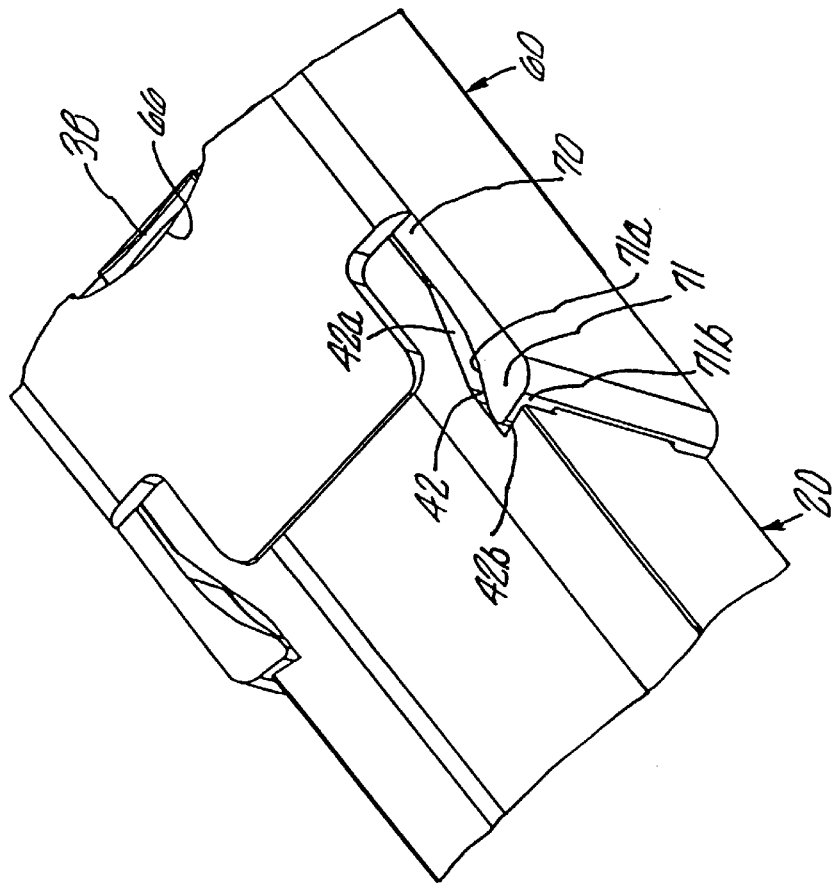
Fig. 6A
Fig. 6B

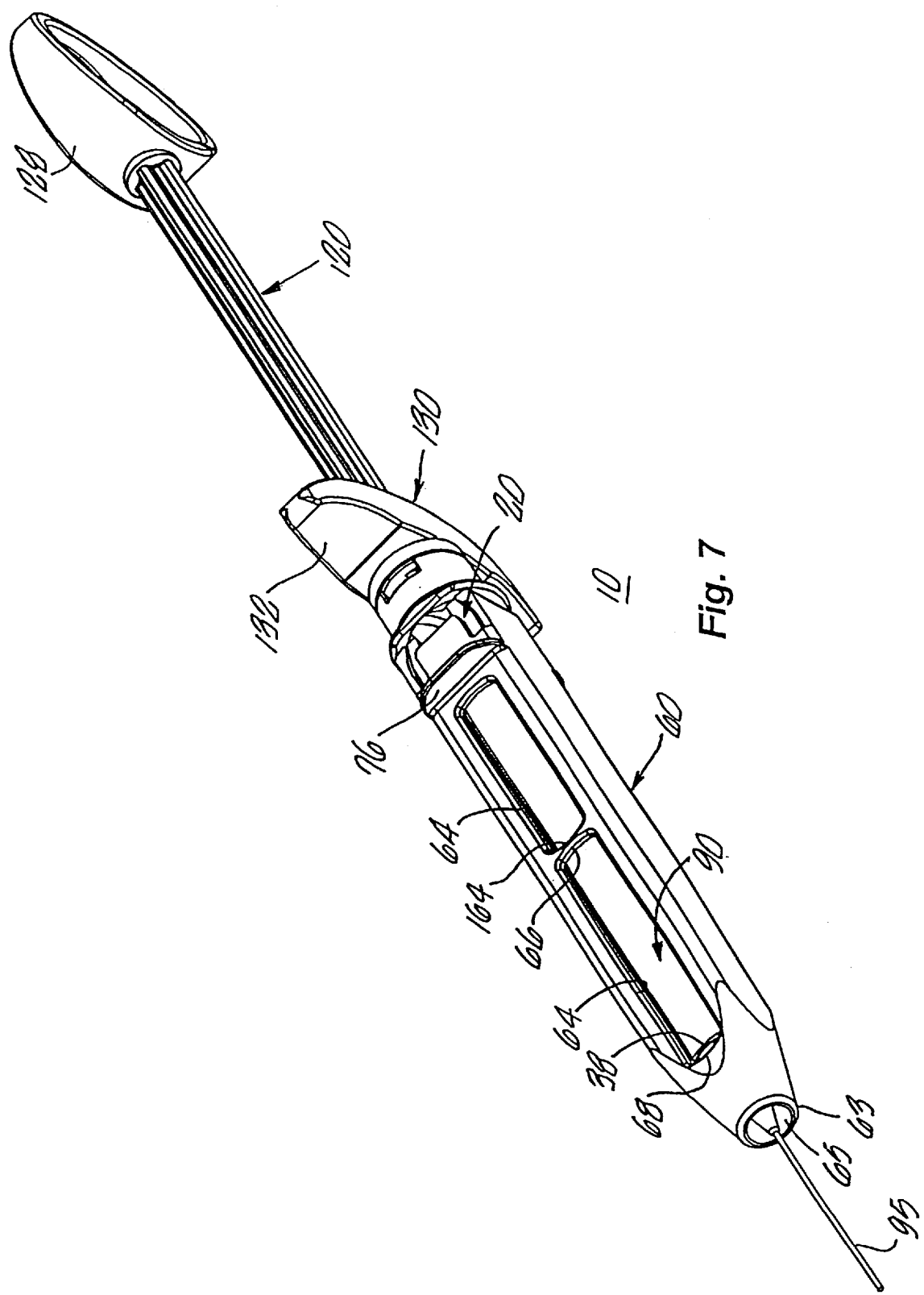

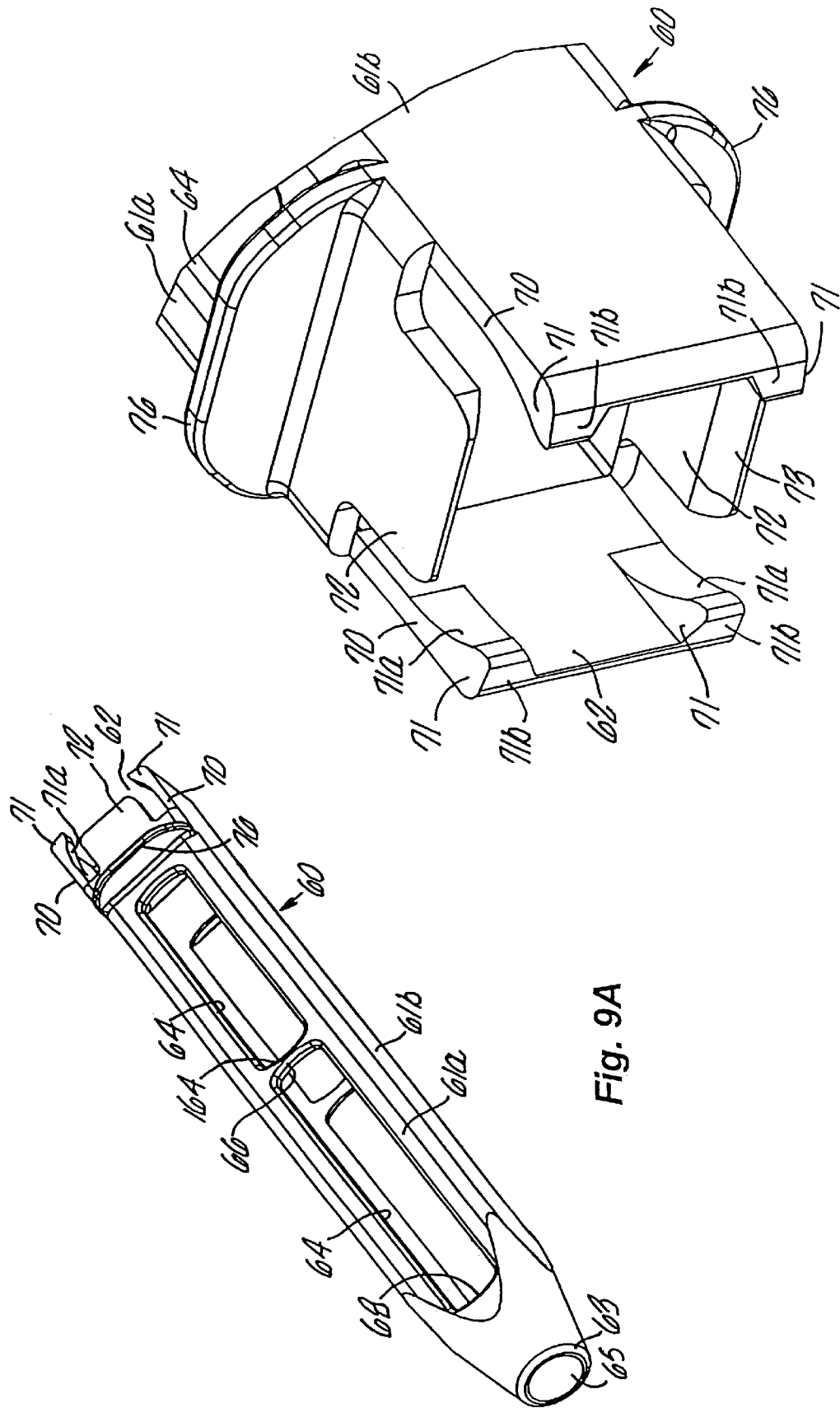

DISPOSABLE SELF-SHIELDING UNIT DOSE SYRINGE GUARD

FIELD OF THE INVENTION

The present invention relates generally to syringes, and more particularly to an improved syringe guard for a unit dose ampule or syringe and including a shield for covering the needle thereof after medication is dispensed from the syringe.

BACKGROUND

Medication is often dispensed using a unit dose cartridge, such as an ampule or syringe, and a syringe holder or adapter. The cartridge is typically a barrel having a needle at one end and a piston at the other end. Alternatively, the cartridge may include a rubber stopper instead of a needle, or may include a plunger assembly attached to the piston. The syringe adapter is typically a hollow body adapted to hold the cartridge, including a plunger to engage and move the piston in the cartridge.

Because of the threat of communicable diseases, a number of syringes and adapters have been developed to prevent accidental needle sticks or inadvertent reuse of needle devices. Many of these devices, however, are not easy to use or are complicated to manufacture, resulting in less effective disposable syringe devices.

For example, U.S. Pat. No. 5,569,211 discloses a syringe that allows the needle of the syringe to be withdrawn into the barrel of the syringe after medication is dispensed from it. This device, however, is a specially designed substitute for a conventional syringe, and cannot be used to hold commercially available unit dose cartridges.

U.S. Pat. No. 5,522,812 discloses a complicated syringe shield device for holding a conventional ampule not having its own needle. The device has a number of complicated parts, including a cylindrical body, a double needle assembly, a cylindrical shield, a special collar piece allowing the shield to be drawn over the needle and locked, and a plunger assembly, resulting in a device that is potentially difficult and expensive to manufacture. The device also requires two hands to operate, one to hold the body, and one to rotate the shield into the locked position, causing inconvenience to the medical professional using the device.

Another consideration with unit dose cartridges is that they are often made from glass, particularly for holding certain vaccines or biotech drugs where concern about micro-organisms or other contaminants is most critical. Glass cartridges are very fragile and often break during transportation or use. Some existing adapters may not adequately protect the cartridge contained therein from such risks. Others provide greater protection for the cartridge, but may obstruct the professional's view of the cartridge when the device is being used, hampering monitoring of the medication being delivered.

Therefore, there is a need for an improved safety syringe which is inexpensive and simple to manufacture.

In addition, there is a need for a safety syringe adapter which provides improved protection for the cartridge therein, but allows effective observation of the cartridge and the medication being dispensed.

SUMMARY OF THE INVENTION

The present invention is directed to a guard or adapter for a medical cartridge, such as a unit dose ampule or syringe, that is used to inject medication or other drugs into a patient. Generally, the guard comprises two parts, namely a housing or body for receiving and holding the cartridge, and a protective case or shield slidably attached to the body. In addition, for a cartridge provided without its own plunger, an embodiment of the guard includes a plunger assembly that is attached to the body. The various parts are generally molded from a suitable plastic, preferably synthetic resinous polymers of butadiene and styrene or polycarbonate, having a clear or opaque finish, which may be colored, such as a latex color or a flesh tone.

The body generally comprises two elongate rails or similar structures defining a substantially rectangular shape, having a cavity therein adapted to receive a medical cartridge. The body has an open proximal end communicating with the cavity, a distal end with an opening through it, and possibly a collar molded to the distal end.

The protective case or shield is a tubular member adapted to slidably fit on the body, having open proximal and distal ends. One or more elongate windows are formed in the shield, allowing observation of the cartridge held within the body. One or more windows, preferably the same windows used for viewing the cartridge, also cooperate with a stop tab or tabs molded on the body, thereby limiting the relative sliding relationship of the shield and the body. In addition, the shield includes a set of detents, preferably comprising a pair of detent arms and protruding detents molded into the proximal end of the shield. The detents cooperate with one or more sets of detent pockets molded into the body to lock the shield in relation to the body.

The shield is generally provided pre-assembled on the body, preferably by inserting the body into the shield until the stop tabs on the body communicate with the elongate windows on the shield. The shield may then slide in relation to the body between a proximal or unguarded position and a distal or guarded position, defined by the length of the windows on the shield. The guard is generally provided with the shield in the proximal or unguarded position, wherein the stop tabs abut the distal edges of the windows. In the unguarded position, the detents on the shield preferably engage a set of proximal detent pockets on the body, holding the shield in relation to the body.

Generally, after the cartridge in the guard has been used to deliver its medication, the shield is moved distally until it reaches the guarded position. In the guarded position, the stop tabs on the body abut the proximal edges of the windows, preventing further distal movement. As the shield is moved, the detents on the shield leave the proximal detent pockets, preferably because of sloping edges on the proximal detent pockets, and slide along the body until they enter a set of distal detent pockets when the shield reaches the guarded position. The distal detent pockets preferably have blunt edges, which prevent the shield from being returned proximally, and thereby substantially lock the shield in the guarded position for disposal.

In a first preferred embodiment, the guard comprises only two parts, namely a body and a shield, which are pre-assembled in the unguarded position ready to receive a cartridge. In this embodiment, the body includes a finger grip molded onto its proximal end, preferably defining a "T" shape, having locking detents formed on the finger grip. A cartridge, preferably and typically a conventional unit dose syringe including a needle and needle cover on its distal end and a plunger on its proximal end, is inserted into the proximal end of the body until it is fully encapsulated within the cavity. Once fully inserted, the proximal end of the cartridge engages the locking detents on the finger grip, substantially permanently locking the cartridge into the guard. Once locked into the guard, the needle and its cover on the cartridge extend through the distal openings in the body and shield and beyond their distal ends.

After medication is dispensed, the shield is slid into the guarded position, generally using only one hand. During use, the index and middle fingers are generally placed on the finger grip adjacent the shield, while the thumb directs the plunger on the cartridge. To move the shield, the thumb and ring finger are moved to the finger grip to hold the body. The index and middle fingers hold the sides of the shield and move it distally, thereby sliding the shield until it is locked in the guarded position.

In a second preferred embodiment, the guard includes a plunger assembly, in addition to the body and shield. The plunger assembly generally comprises a plunger, preferably including a thumb ring or a "T" handle, and a finger grip section into which the plunger is pre-assembled. The finger grip section and the proximal end of the body include members for locking the finger grip section to the body. Preferably, the finger grip section has locking detents thereon, and the proximal end of the body includes an annular-shaped collar having tapered pockets therein adapted to receive the locking detents.

The body and shield are generally provided pre-assembled in the unguarded position, as previously described, with the plunger assembly furnished separately. A cartridge, preferably a unit dose ampule having a needle and needle cover on its distal end and a piston in its proximal end, is inserted into the proximal end of the body until it is fully encapsulated within the cavity. Once fully inserted, the plunger assembly is attached to the body, by aligning the locking detents on the finger grip section with the tapered pockets in the collar. The locking detents are inserted into the pockets until they engage, substantially permanently locking the cartridge into the guard. As before, the needle on the cartridge extends beyond the distal ends of the shield and body, exposing the needle and cover ready for use. The plunger is attached to the piston on the cartridge, such as by a threaded bore on the distal end of the plunger which is adapted to screw into a threaded nipple on the piston. The device is then ready to be used to deliver medication to a patient. After medication is dispensed, the shield is slid into the guarded position, as with the first embodiment, generally requiring only one hand. The finger grip section is held with two or more fingers, while the index and middle fingers slide the shield distally until it is locked in the guarded position.

As will be understood, the present invention provides an improved medical cartridge guard, that may include as few as two parts, but generally has no more than four parts. The device may be used for a wide variety of conventional prepackaged medications or drugs, such as anesthesia or vaccines, for use within the medical and/or dental fields, where the cartridge is generally disposed of after a single use. Because the device is relatively simple, the parts may be provided in standard configurations. For example, a single shield design may be provided that fits on a variety of bodies for receiving cartridges made by different manufacturers. Thus, the guard may be more easily mass produced, reducing manufacturing costs, and thereby providing a more competitively priced disposable syringe guard.

In addition, the rectangular configuration of the present device provides improved rigidity, thereby affording greater protection to the cartridge held in the guard. Although the cartridge is fully encapsulated within the guard, the windows in the guard allow the medical or dental professional to effectively monitor the cartridge and the medication being delivered.

Finally, the slidable shield and cooperating detents allow the user to operate the guard using only one hand, thereby allowing their other hand to be free to perform other necessary tasks, such as restraining a young patient or providing improved access to the target region for the needle. Once the shield is locked in the guarded position, the device may be disposed of safely if used properly, substantially eliminating concerns that the needle may become exposed and cause an accidental stick.

Accordingly, it is a principal object of the present invention to provide an improved unit dose syringe device that is easy to manufacture and convenient to use.

It is also an object to provide an improved syringe guard that affords improved protection for the cartridge encapsulated therein but still allows effective monitoring of the medication being dispensed.

Other objects and features of the present invention will become apparent from consideration of the following description taken in conjunction with the accompanying drawings.

BRIEF DESCRIPTION OF THE DRAWINGS

For a better understanding of the invention, and to show how it may be carried into effect, reference will be made, by way of example, to the accompanying drawings, in which:

FIGS. 6A and 6B are perspective views of the syringe guard holding a syringe, with the shield locked in a guarded position after medication has been dispensed from the syringe.

FIG. 7 is a perspective view of another preferred embodiment of the syringe guard holding a unit dose cartridge, with the shield in the unguarded position, and ready to be used to deliver medication to a patient.

FIGS. 9A and 9B are perspective views of the shield of the syringe guard of FIG. 7.

DETAILED DESCRIPTION OF THE PREFERRED EMBODIMENTS

Figure 1:
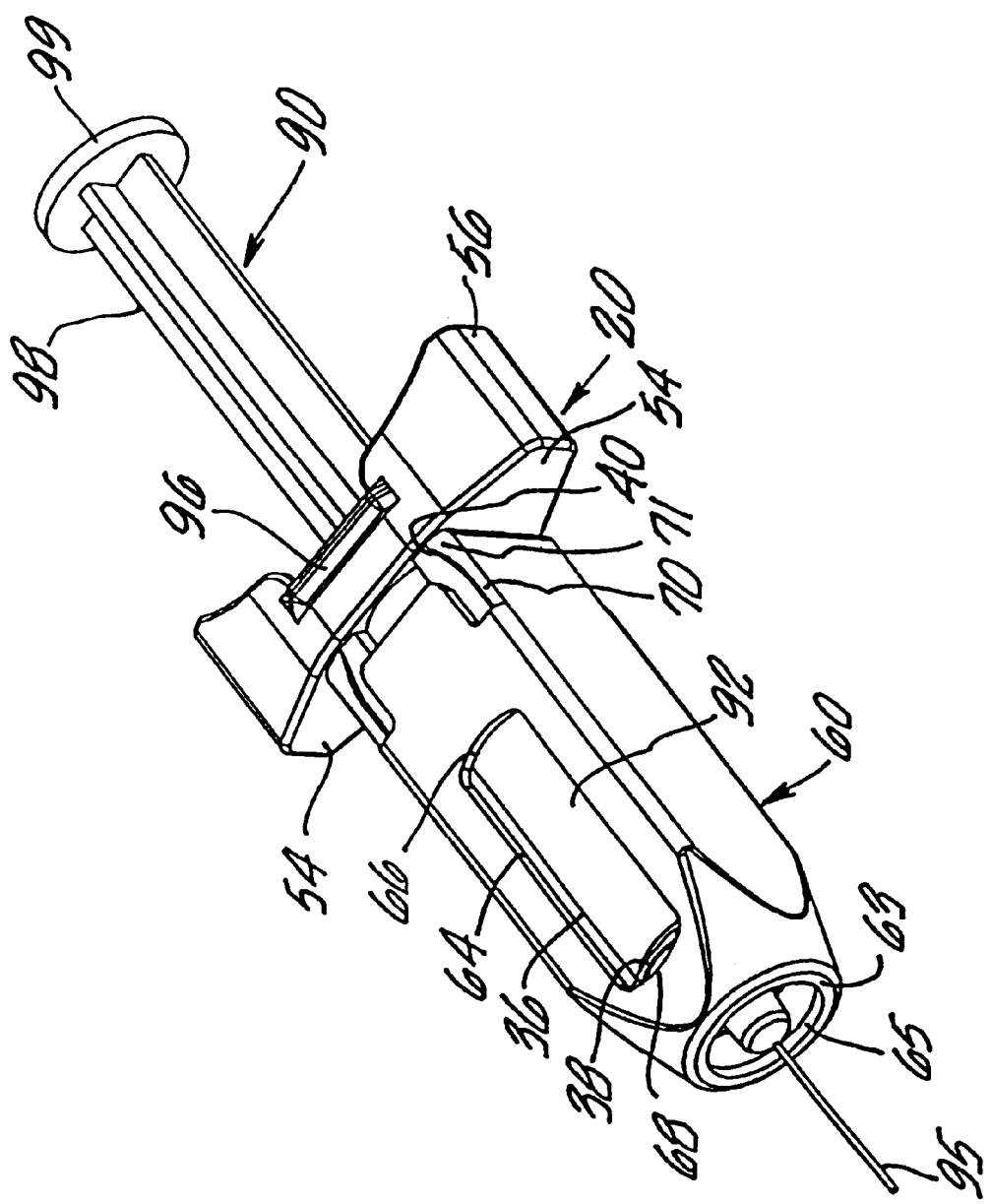
FIG. 1 is a perspective view of a first preferred embodiment of the syringe guard of the present invention, holding a unit dose syringe.

Turning to the drawings, FIG. 1 shows a first preferred embodiment of the present invention, namely a syringe guard 10 for holding a unit dose syringe 90. Generally, the guard 10 comprises two parts, namely a housing or body 20 for receiving and holding the cartridge or syringe 90, and a protective case or shield 60 slidably attached to the body 20. Both the body 20 and the shield 60 are generally molded from plastic, preferably synthetic resinous polymers of butadiene and styrene or polycarbonate, and are preferably clear and substantially colorless. Alternatively they may be translucent or opaque, and may be colored, such as a latex color, or a flesh tone, such as off-white, brown, or black.

Figure 2A:
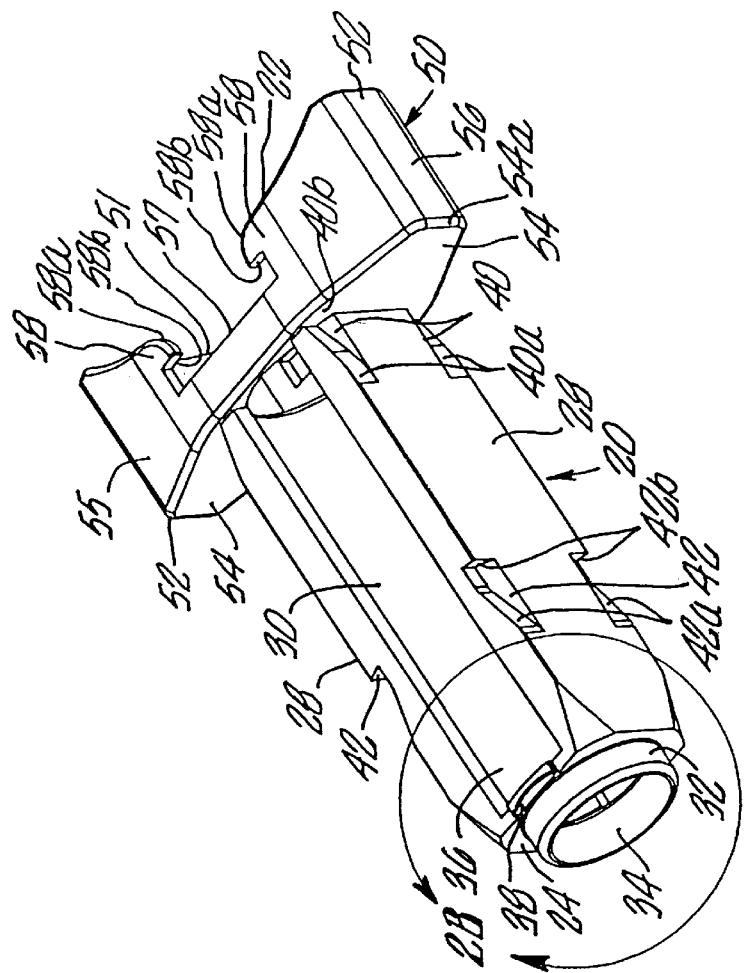
FIGS. 2A, 2B and 2C are perspective views of the body of the syringe guard of FIG. 1.
Figure 2B:
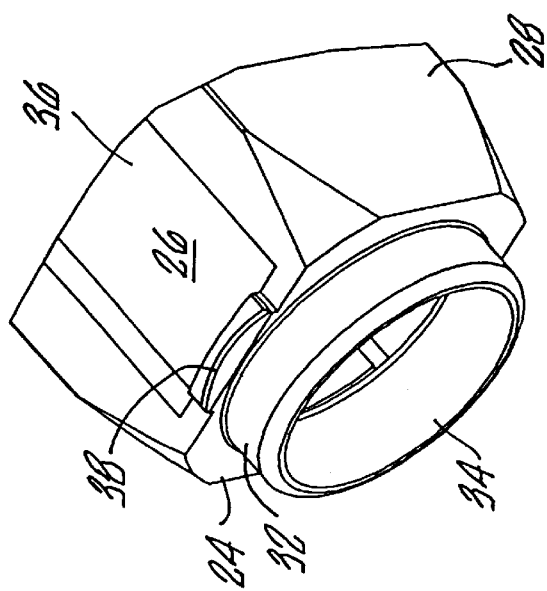
Figure 2C:
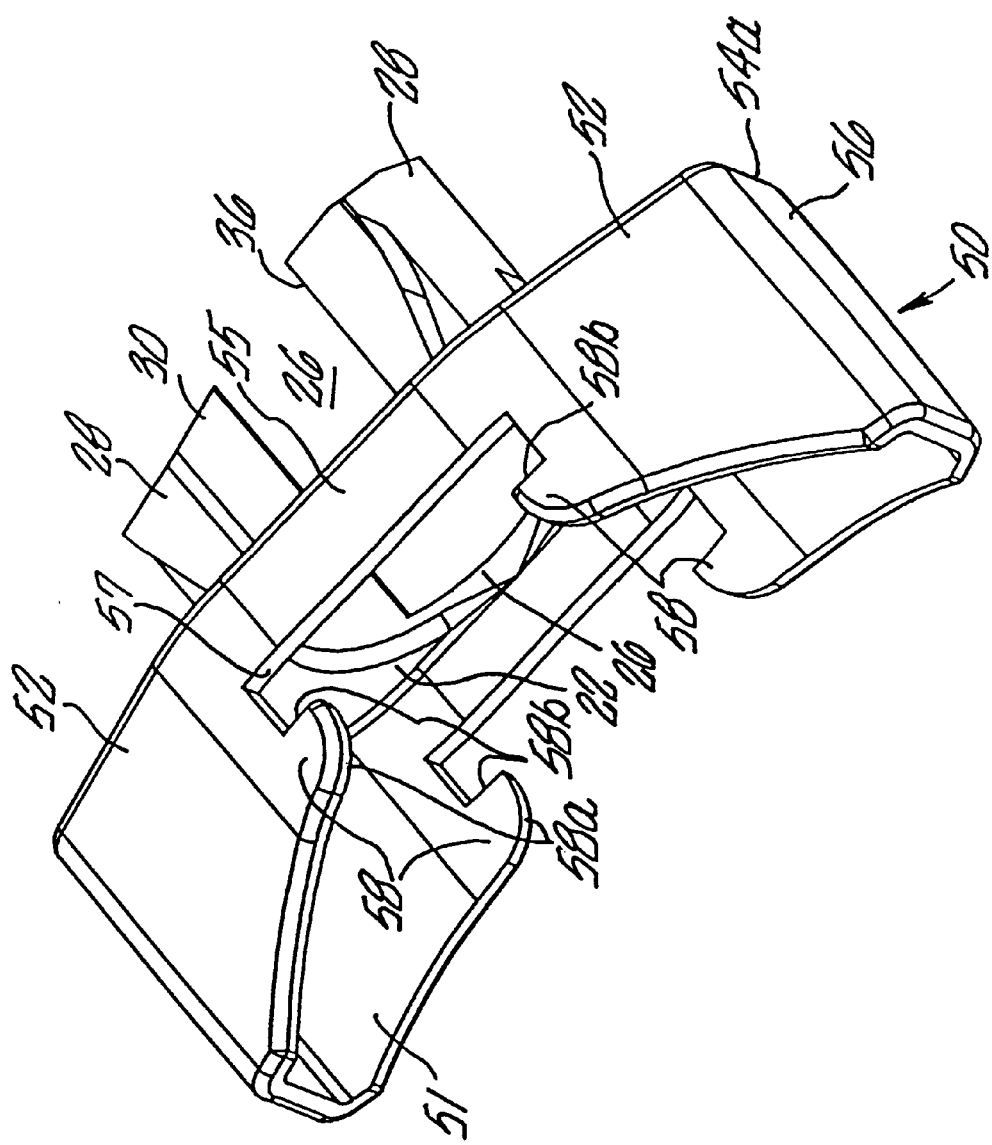

Turning to FIGS. 2A, 2B and 2C, the body 20 is an elongate member, preferably having a substantially rectangular cross-section, comprising two side rails 28, an open proximal end 22, and an open distal end 24. The rectangular shape is preferred as it provides superior rigidity, protecting the syringe therein from lateral forces that might otherwise damage it, particularly if the syringe is made of glass. In addition, the body 20 has a collar 32 on the distal end 24, and a finger grip 50 on the proximal end 22, both attached to or preferably integrally molded onto the body 20. Alternatively, instead of comprising side rails 28, the body 20 may comprise a substantially rectangular body having four side walls (not shown).

The two side rails 28 generally have a "C" shape and define a cavity 26 in the body 20, the cavity 26 extending from the proximal end 22 to the distal end 24 of the body 20. The inside surface 30 of the rails 28 is preferably concave, conforming substantially to the outer diameter of a standard unit dose syringe. Alternatively, if the side rails 28 have a flat or "C" channel inside surface 30, guide rails (not shown) or the like may be provided on the inside surface 30 to direct the syringe 90 into the cavity 26 and hold it, thereby substantially preventing lateral movement which may damage the syringe 90.

As shown in FIGS. 2A and 2C, the finger grip 50 generally comprises a pair of wing-like members 52 molded onto the proximal end 22 of the body 20, thereby generally defining a "T" shape. Each wing-like member 52 includes a distal surface or finger ledge 54, and an outer gripping surface 56 extending proximally from the outer edge 54a of the finger ledge 54. The outer gripping surface 56 may include a lip (not shown) protruding radially from its proximal end, if desired to improve the hold on the finger grip 50. Lateral surfaces 55 extend proximally from the finger ledges 54 between the gripping surfaces 56, thereby defining an open proximal end 51 communicating with the cavity 26 in the body 20. The lateral surfaces 55 of the finger grip 50 include a plurality of locking detents 58 partially defining an aperture or slot 57 for holding the cartridge (not shown in FIGS. 2A and 2B) inserted into the cavity 26, as will be described further below.

Turning to FIG. 2B, the collar 32 extending from the distal end 24 preferably has a substantially annular shape, including an opening 34 extending therethrough adapted to allow the needle and needle cover on the cartridge (not shown) in the cavity 26 to extend beyond the body 20. The opening 34 preferably has a diameter smaller than the cavity 26, such that the distal end 24 substantially retains the cartridge inside the cavity 26, preventing distal movement. Alternatively, the distal end 24 may be tapered or otherwise partially obstructed, as long as it engages the distal end of the cartridge, preventing distal movement of the cartridge, and does not substantially interfere with the needle and cover extending beyond the distal end 24.

The side rails 28 define two elongate openings or windows 36 extending longitudinally between the finger grip 50 and the distal end 24, allowing observation of the cartridge held in the body 20. Alternatively, if a four-walled body is provided, an elongate opening or window may be integrally formed in one or more of the side walls, preferably in two walls on opposite sides of the body 20. The body 20 also includes one or more stop tabs 38 attached or molded directly to the body 20. Preferably, stop tabs 38 are molded onto the body 20 on two opposite sides of the distal end 24 of the body 20.

The body 20 also includes one or more sets of detent pockets, preferably having a set of proximal detent pockets 40 adjacent the finger grip 50, and a set of distal detent pockets 42 at a more distal location on the body 20. The detent pockets lock the relative movement between the shield 60 and body 20, as is explained more fully below.

Figure 3A:
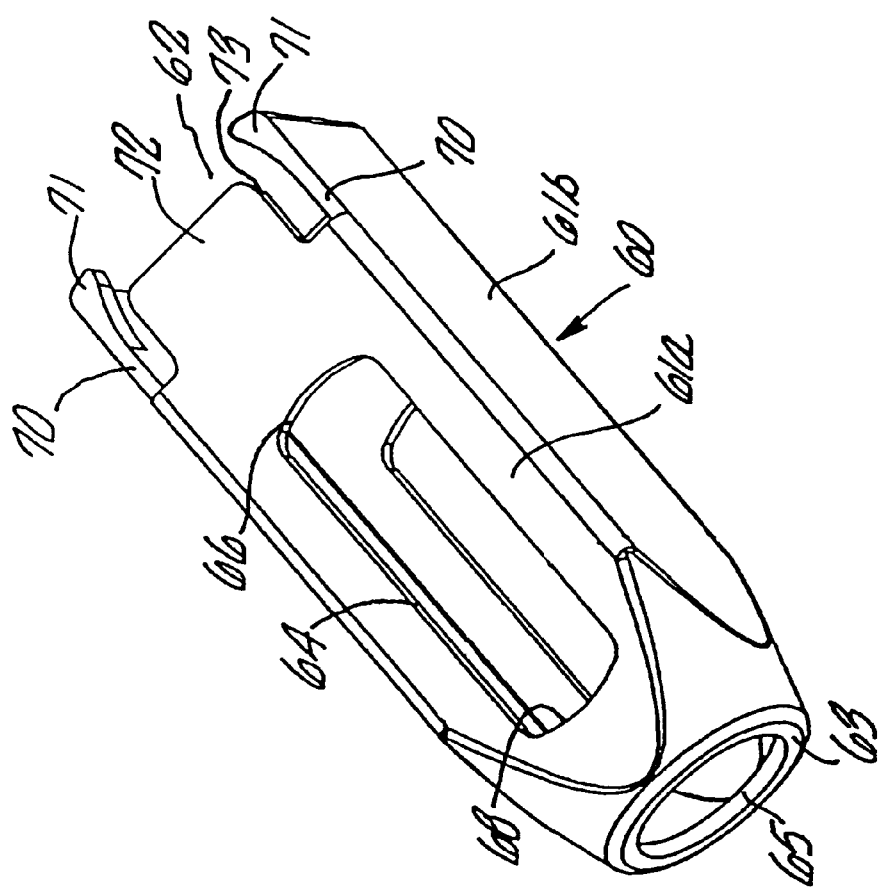
FIGS. 3A and 3B are perspective views of the shield of the syringe guard of FIG. 1.
Figure 3B:
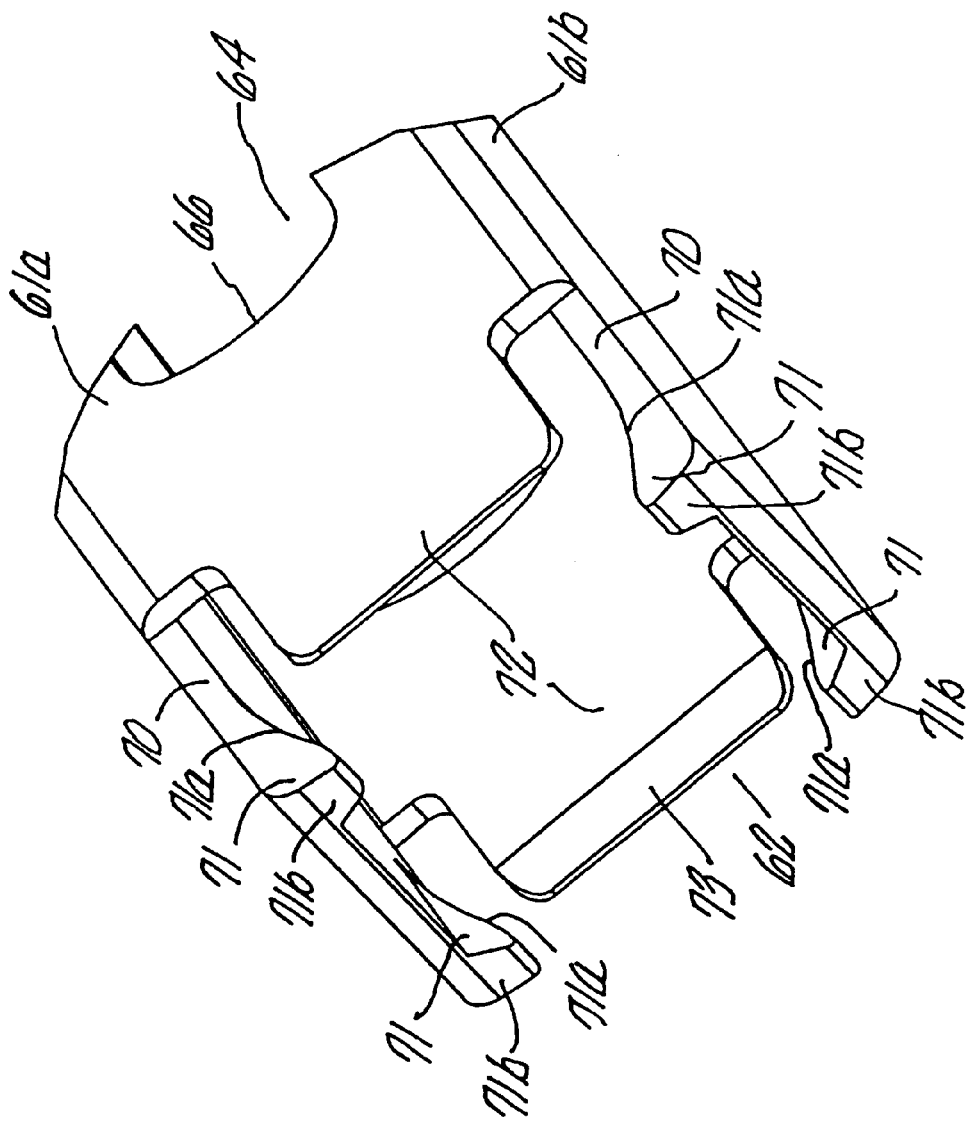

Turning now to FIGS. 3A and 3B, the protective case or shield 60 is a tubular member adapted to slidably fit on the body 20, preferably having a substantially rectangular interior shape which conforms to the shape of the body 20. The shield 60 includes four side walls 61a, 61b, an open proximal end 62, and an open distal end 63. The shield 60 has a pair of detent arms 70 and a plurality of detents 71 attached to or preferably integrally molded directly into the side walls 61b. Assembly tabs 72 with sloping or ramped interior surfaces 73 are molded into and extend proximally from the side walls 61a.

At least one wall 61a, preferably the two opposite walls 61a, includes an elongate opening or window 64 therethrough. The window 64 allows observation of the cartridge in the body 20, and also provides a traveling slot for the stop tab 38 on the body 20. The window 64 has a proximal edge 66 and a distal edge 68 defined by the wall 61a which limit the relative movement of the shield 60 to the body 20, as will be explained more fully below. Alternatively, the window 64 may be divided by a cross-member (not shown) molded into the wall 61a which extends transversely across the window 64 if it is desired to further limit the movement of the shield 60.

Optionally, the side walls 61a, 61b may include wings, a ring or similar finger holds (not shown) extending radially from the shield 60 to ease movement of the shield 60 in relation to the body 20. In addition, the side walls 61b may provide a flat surface onto which a label may be applied or an embossed pattern may be molded, possibly including a name or a logo.

Figure 4:
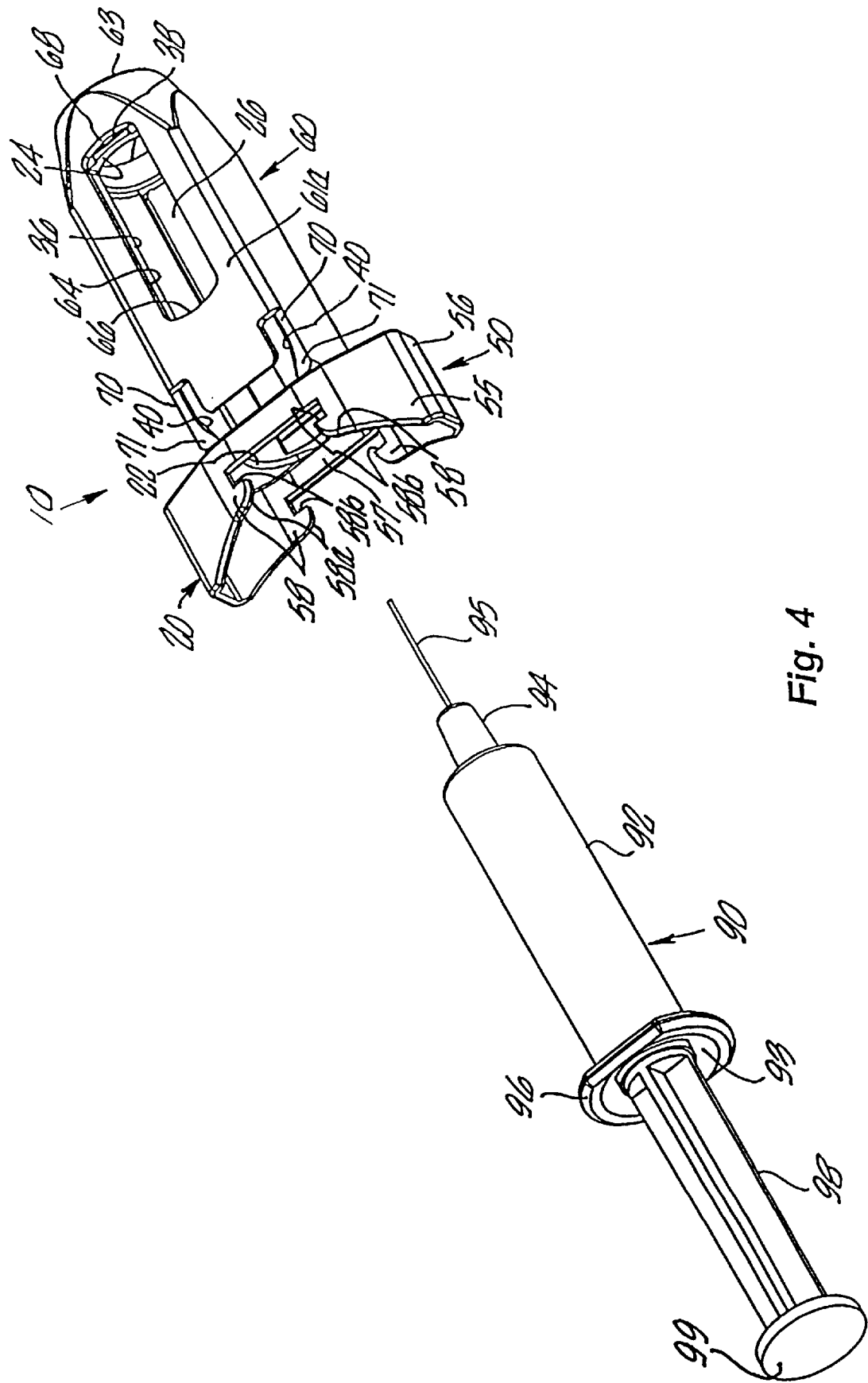
FIG. 4 is a perspective view of the pre-assembled syringe guard about to receive a conventional unit dose syringe therein.

Turning to FIG. 4, the guard 10 is normally provided with the body 20 and shield 60 pre-assembled as shown. To assemble the guard 10, the distal end 24 of the body 20 (see FIG. 2A) is inserted into the open proximal end 62 (see FIG. 3A) of the shield 60, with the window 36 in the body 20 aligned with the side wall 61a of the shield 60 having the window 64 therein. As the body 20 is inserted, the stop tab 38 (the stop tab and window not shown on the opposite side operate substantially the same way) engages the tapered interior edge 73 of the assembly tab 72 on the shield 60 (see FIG. 3B), allowing the stop tab 38 to pass under the wall 61a. After the stop tab 38 passes under the wall 61a, it then enters the window 64 where it may freely travel.

Together, the stop tab 38 and window 64 allow the shield 60 to slidably move in relation to the body 20, but substantially define the limits of that relative movement. The shield 60 may slide proximally and distally until the stop tab 38 abuts a distal edge 68 and a proximal edge 66, respectively, of the window 64. Specifically, when the stop tab 38 engages the distal edge 68 of the window 64, as shown in FIG. 4, the shield 60 is in a proximal or unguarded position. When the stop tab 38 engages the proximal edge 66 of the window 64, as shown in FIGS. 6A and 6B, the shield is in a distal or guarded position.

Figures 5A, 5B:
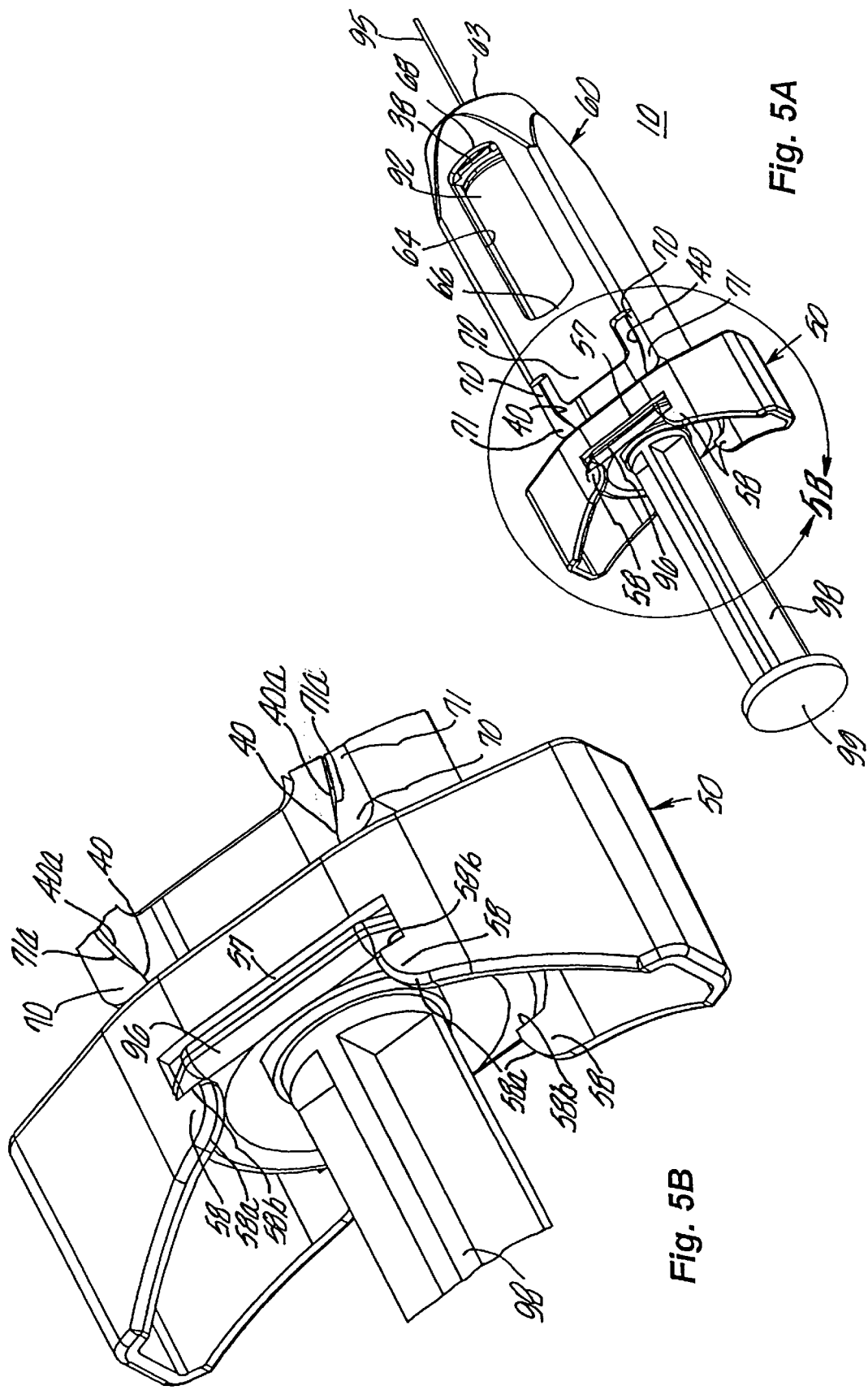
FIGS. 5A and 5B are perspective views of the syringe guard holding a syringe, with the shield in an unguarded position, and ready to be used to deliver medication to a patient.

Referring to FIGS. 5A and 5B, when the stop tab 38 abuts the distal edge 68 of the window 64, the cooperating detents 71 and proximal detent pockets 40 operate to hold the shield 60 in the unguarded position. The sloping distal edges 71a of the detents 71 engage the sloping distal edges 40a of the proximal detent pockets 40 on the body 20, thereby preventing the shield 60 from moving distally.

Turning again to FIG. 4, once assembled, the guard 10 is ready to receive a cartridge, such as a conventional unit dose syringe 90. The syringe 90 generally comprises a barrel 92, a distal end 94 including a hypodermic needle 95, a needle cover (not shown), a proximal end 93 having a lip 96, and a plunger 98. The distal end 94 of the syringe 90 is inserted into the open proximal end 22 of the body 20. The syringe 90 enters the cavity 26 and progresses distally until the distal end 94 of the syringe 90 engages the distal end 24 of the body 20. The distal end 94 of the syringe may simply abut the distal end 24 of the body 20, or alternatively the distal end 94 of the syringe 90 may partially enter the opening 34 and engage the collar 32, thereby providing additional protection from lateral movement of the syringe 90 (FIGS. 1 and 6A).

As the syringe 90 becomes fully encapsulated within the cavity 26, the lip 96 on the proximal end 93 of the syringe 90 contacts the locking detents 58 on the finger grip 50. The locking detents 58 have tapered proximal edges 58a, allowing the syringe to be directed further distally, the lip 96 moving the locking detents 58 aside and entering the slot 57. As is shown in FIGS. 5A and 5B, the locking detents have blunt distal edges 58b which prevent the syringe 90 from being removed proximally from the slot 57, thereby substantially permanently locking the syringe 90 into the body 20, an important feature of the present invention.

Referring to FIGS. 1 and 5A, once the syringe 90 is locked into the guard 10, the needle 95 and its cover (not shown) extend through the opening 34 on the collar 32 and the opening 65 on the distal end 63 of the shield 60. The syringe 90 may then be used in a conventional manner to deliver medication in the barrel 92. The medical professional typically holds the syringe by placing their index finger on a finger ledge 54, their middle finger on the other finger ledge 54, and their thumb on the end 99 of the plunger 98. The cover (not shown) is removed, the needle 95 is inserted into the patient, and the medication is delivered by directing the plunger 98 distally with the thumb. As can be seen from FIGS. 1 and 5A, the windows 64 and 36 provide constant observation of the barrel 92 of the syringe 90, allowing the user to closely monitor delivery of the medication.

After the medication is dispensed, the needle 95 is withdrawn from the patient, and the self-shielding feature of the guard 10 is engaged. The user holds the body, typically by placing his ring finger on the gripping surface 56 adjacent his middle finger, and moving his thumb from the plunger 98 to the other gripping surface 56. The index and middle fingers, already adjacent the side walls 61b of the shield 60, grip the walls 61b and are moved distally, thereby sliding the shield 60 distally until it reaches the guarded position, shown in FIG. 6A.

Because the cooperating detents 71 and detent pockets 40 hold the shield 60 in the unguarded position, force must be applied to move the shield 60 distally. As previously discussed, the detents 71 have sloping distal edges 71a and blunt proximal edges 71b (FIG. 3B), and similarly, the proximal detent pockets 40 have sloping distal edges 40a (FIG. 5B) and blunt proximal edges 40b (FIG. 2A). Because of the sloping distal edges 71a, 40a, the engagement between the detents 70 and the proximal detent pockets 40 may be overcome by pushing the shield 60 distally in relation to the body 20. The detent arms 70 move radially as the detents 71 move distally up the sloping edges 40a until the detents 71 leave the detent pockets 40. The shield may then be moved freely, the stop tab 38 traveling along the window 64, until the stop tab 38 abuts the proximal edge 66 of the window 64, reaching the guarded position.

As shown in FIG. 6A, because of the predetermined location of the distal detent pockets 42, when the stop tab 38 reaches the proximal edge 66 of the window 64, the detents 71 substantially simultaneously enter the distal detent pockets 42. The blunt proximal edges 71b of the detents engage the blunt proximal edges 42b of the distal detent pockets 42, thereby preventing the shield 60 from being moved proximally. Furthermore, because the stop tab 38 abuts the proximal edge 66 of the window 64, the shield 60 may not be moved further distally. Thus, the shield 60 is thereby substantially permanently locked in the guarded position.

As can be seen from FIG. 6A, when the shield 60 is moved distally into the guarded position, the distal end 63 of the shield 60 passes over the needle 95, covering the needle 95. Once the shield 60 is locked in the guarded position, the needle 95 is no longer accessible, thereby substantially eliminating the risk of accidental sticks, and preventing reuse of the syringe 90. The guard 10 and syringe 90 may then be disposed of safely.

Turning now to FIG. 7, a second preferred embodiment is shown, namely a syringe guard 10 for holding a unit dose ampule 190 manufactured without its own plunger. Generally, the guard 10 comprises three parts, namely a housing or body 20 for receiving and holding the cartridge or ampule 190, a protective case or shield 60 slidably attached to the body 20, and a plunger assembly 120. As before, the parts are molded from plastic, preferably synthetic resinous polymers of butadiene and styrene or polycarbonate, having a clear, colorless finish, or alternatively a translucent or opaque finish, possibly including a color, such as latex or flesh tone.

Figure 8A:
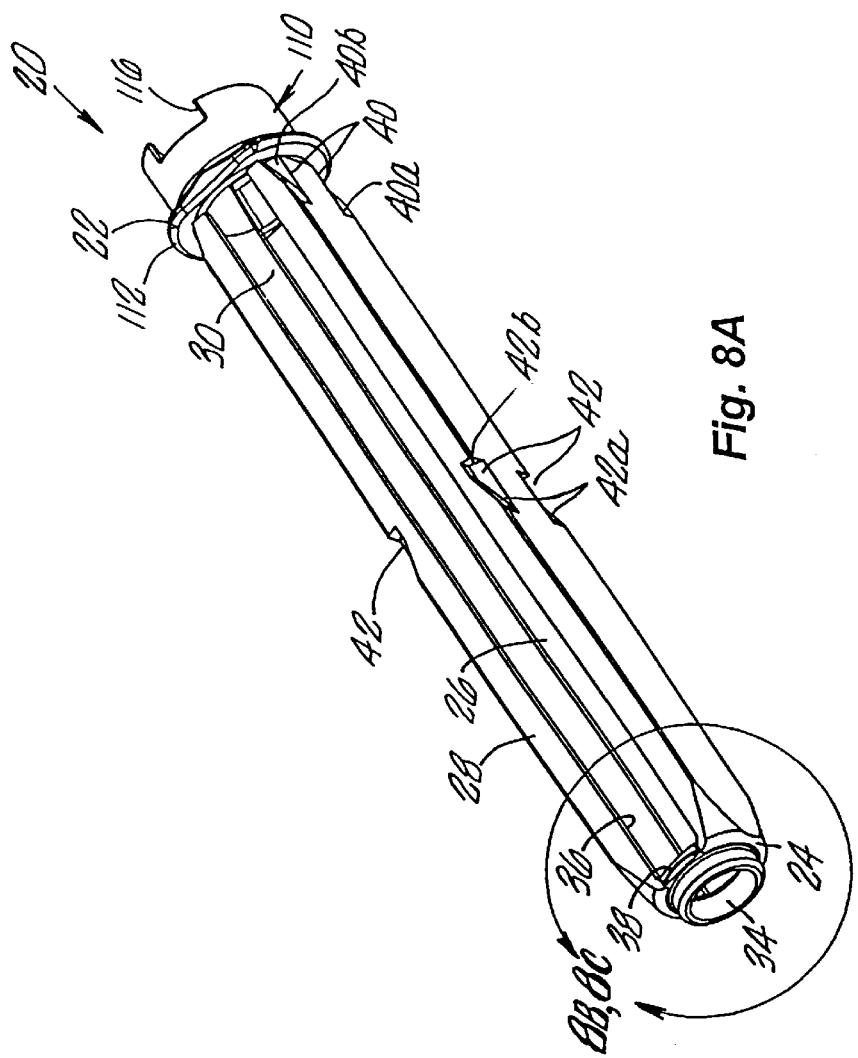
FIGS. 8A, 8B, 8C and 8D are perspective views of the body of the syringe guard of FIG. 7.
Figure 8B:
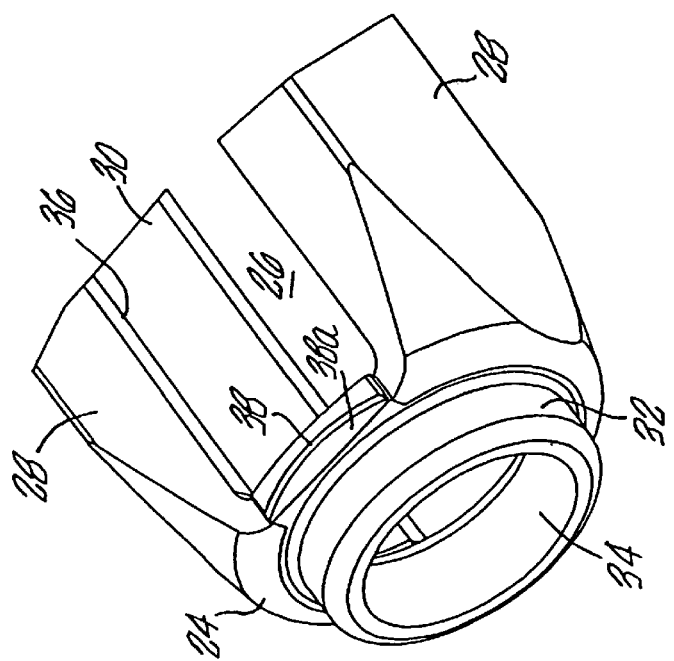
Figure 8C:
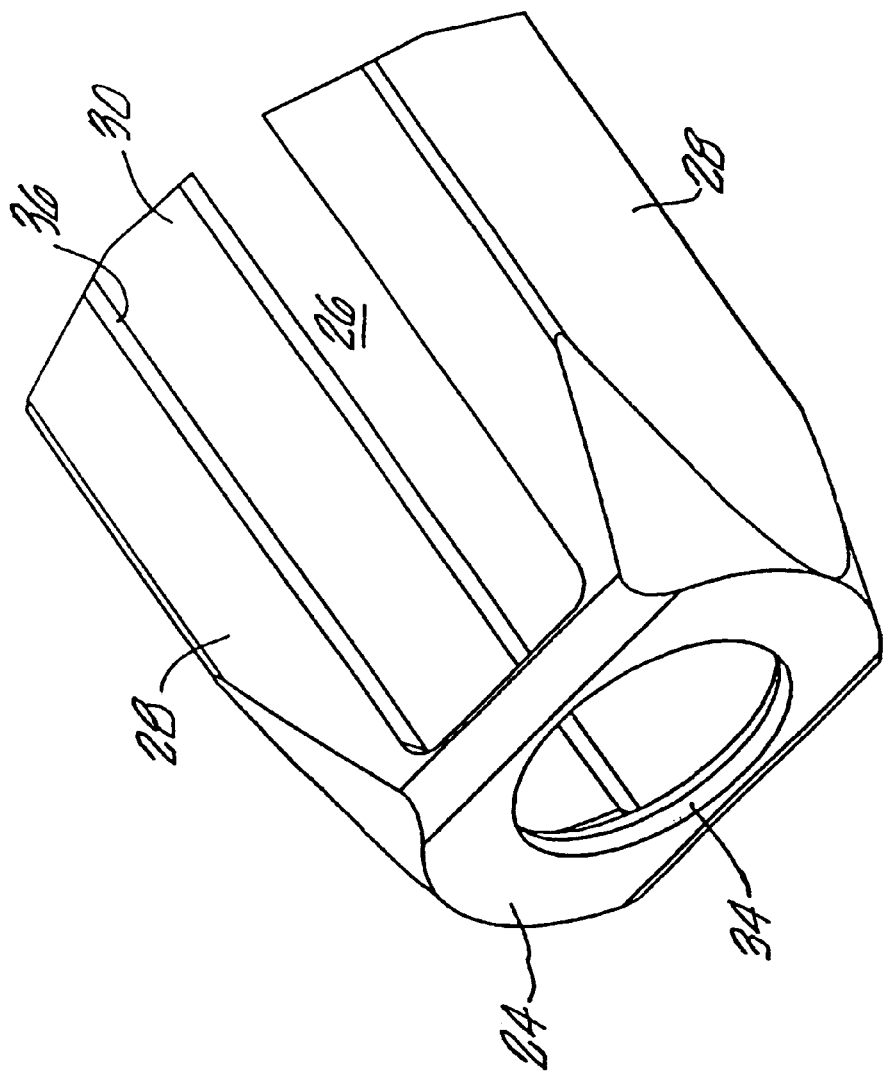

Turning to FIG. 8A, the body 20 has two elongated side rails 28, a proximal end 22 and a distal end 24. As shown in FIG. 8B, a collar 32 is molded directly on the distal end 24 and has an opening 34 therethrough. Alternatively, as in FIG. 8C, it may be appropriate to provide the distal end 24 with the opening 34 formed directly through it and eliminate the collar 32.

The two side rails 28 have concave inside surfaces 30 conforming substantially to the outer diameter of a standard unit dose ampule, thereby defining a cavity 26 in the body 20 for holding the ampule. The outer edges of the side rails 28 define a substantially rectangular cross-section for the body 20, providing a substantially rigid structure for protecting the ampule encapsulated within the body 20. In addition, the side rails 28 define two elongate openings or windows 36 extending between the proximal end 22 and the distal end 24, thereby allowing observation of the ampule (not shown). The body 20 also includes one or more stop tabs 38 molded onto the body 20, preferably on two opposite sides of the distal end 24, and preferably between the window 36 and the collar 32 on two opposite sides of the body 20. Similar to the previous embodiment, the body 20 also includes a set of proximal detent pockets 40 adjacent the finger grip collar 110 (or ring 112), and a set of distal detent pockets 42 at a more distal location on the body 20.

Figure 8D:
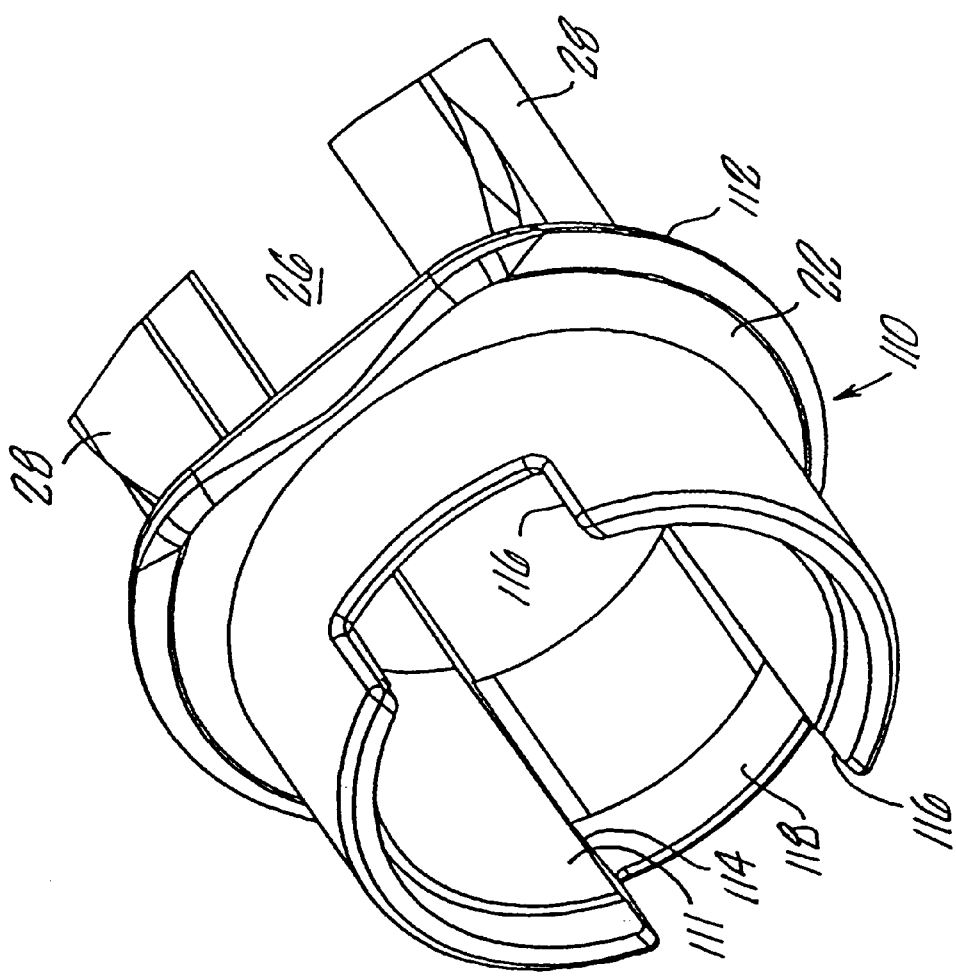

Turning to FIG. 8D, the proximal end 22 of the body 20 includes a finger grip collar 110, preferably molded directly thereon. The finger grip collar 110 has a circular opening 111 extending through it, communicating with the cavity 26 in the body 20. Tapered grooves 114 are formed on the inside the collar 110, defining tapered pockets 118 used to attach the plunger assembly 120 to the body 20. Notches 116 are formed in the collar 110 adjacent the tapered grooves 114 to provide easy orientation during attachment. The collar 110 also includes a finger grip ring 112 which extends radially out from the distal end of the collar 110, allowing the body 20 to be held more easily.

Turning now to FIGS. 9A and 9B, the protective case or shield 60 is a tubular member adapted to slidably fit on the body 20, similar to the shield previously described. The shield 60 includes four side walls 61a, 61b, an open proximal end 62, and an open distal end 63. The shield 60 has a pair of detent arms 70 and detents 71 molded into the side walls 61b. Assembly tabs 72 with tapered interior surfaces 73 are molded into and extend proximally from side walls 61a. Finger holds 76 are molded onto and extend radially from the side walls 61a.

The two opposite walls 61a each include an elongate window 64 which allows observation of the cartridge in the body 20, and also provides a traveling slot for the stop tab 38 on the body 20. Each window 64 has a proximal edge 66 defined by a cross-member 164 and a distal edge 68 defined by the wall 61a. The windows 64 and the stop tabs 38 together limit the relative movement of the body 20 and the shield 60, as previously described.

Figure 10:
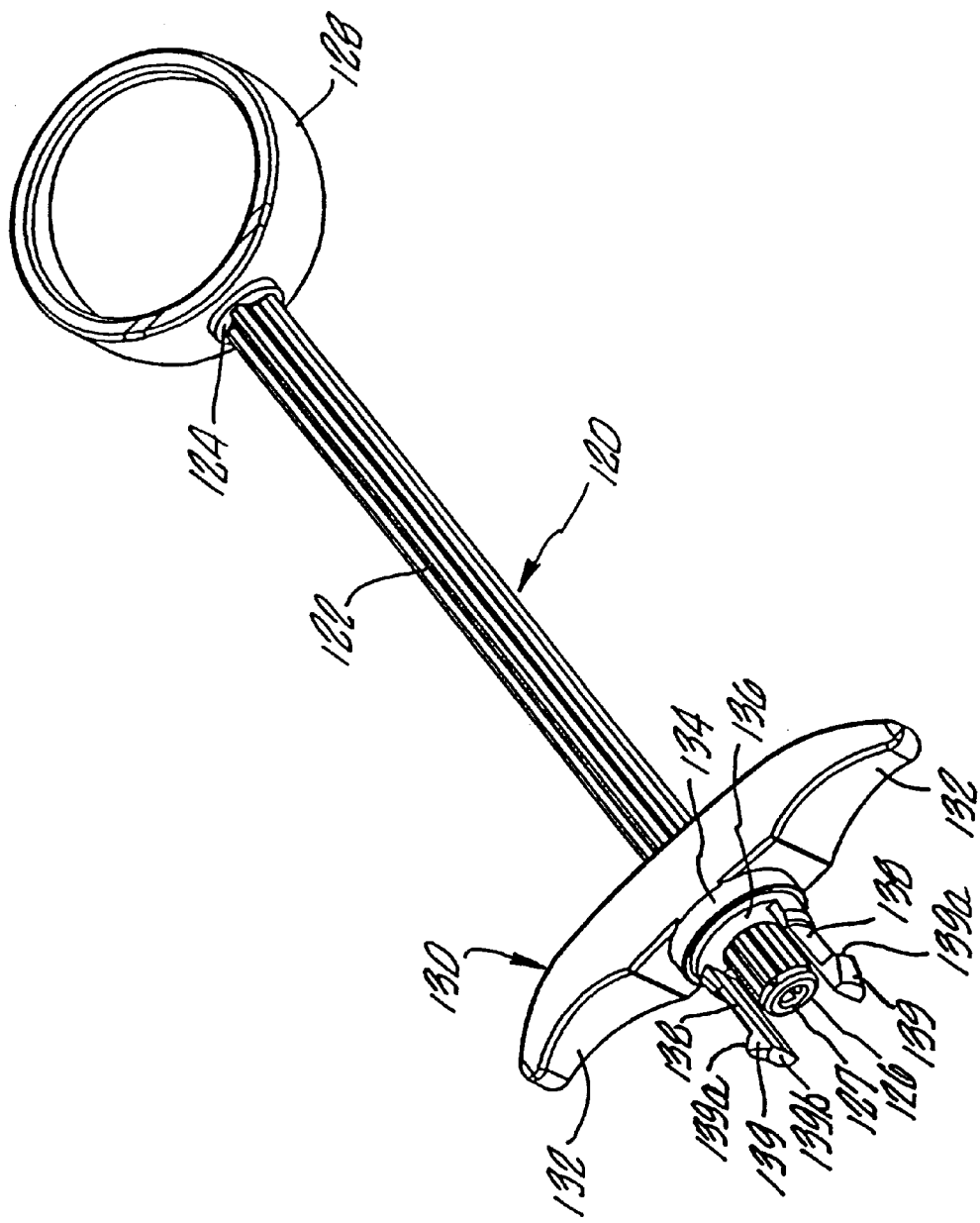
FIG. 10 is a perspective view of the plunger assembly of the syringe guard of FIG. 7.

Referring now to FIG. 10, the plunger assembly 120 is shown as including a plunger 122 and a finger grip section 130. The plunger 122, preferably having a cruciform cross-section, has a thumb ring 128 on its proximal end 124, and a threaded bore 127 on its distal end 126. The threaded bore 127 is a shallow hole having a standard thread pattern, adapted to screw onto the threaded nipple on the piston on a conventional medical ampule. Alternative distal ends may be provided, such as a harpoon, a threaded nipple, an adhesive material, a frictional surface or the like, if appropriate for attaching to the piston of a desired medical cartridge. In addition, alternative proximal ends may be provided, such as a "T" type thumb grip, instead of the thumb ring.

The finger grip section 130 comprises a central hub 134, a pair of finger ledges 132 extending radially from the hub 134, and a pair of fingers 138 extending distally from the hub 134. The hub 134 also has a passage extending axially through it, adapted to receive the plunger 120. The fingers 138 include locking detents 139, which are described more fully below.

Figure 12:
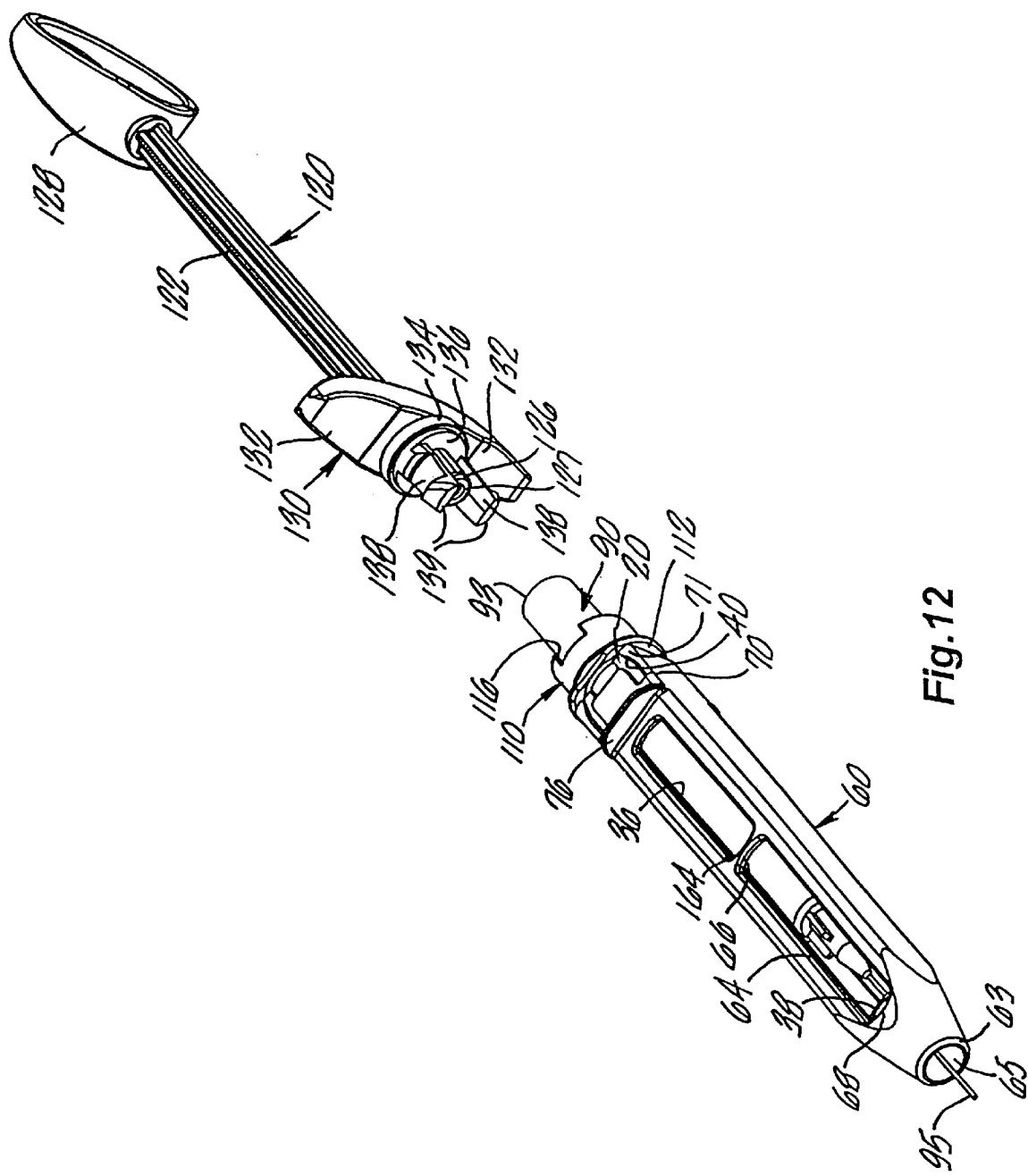
FIG. 12 is a perspective view of the syringe guard with a unit dose ampule partially inserted into the body, and with the plunger assembly aligned and ready to be attached to the body.

Turning to FIG. 12, the guard 10 is normally provided with the body 20 and shield 60 pre-assembled and the plunger assembly loose, as shown. To pre-assemble the body 20 and shield 60, the distal end 24 of the body 20 (see FIG. 8A) is inserted into the proximal end 62 of the shield 60 (see FIG. 9A), with the window 36 in the body 20 aligned with the wall 61a of the shield 60 having the window 64 therein. The stop tab 38 includes a sloped or ramped distal edge 38a that engages the tapered interior edge 73 of the assembly tab 72 (see FIG. 9B), allowing the stop tab 38 to pass under the wall 61a until it enters the proximal portion of the window 64. The ramped distal edge also allows the stop tab 38 to pass under the cross-member 136, until it enters and travels freely in the distal portion of the window 64. The detent arms 70 are directed radially outward to prevent them from engaging the distal detent pockets 42, and then the shield 60 is directed proximally until the detents engage the proximal detent pockets 40, holding the shield in the unguarded position.

Turning to FIG. 10, the plunger assembly 120 is pre-assembled by inserting the distal end 126 of the plunger 122 through the passage 136 in the finger grip section 130. Preferably, tabs (not shown) are provided on the plunger 122 adjacent the distal end 126, preventing the plunger 122 from being proximally removed from the finger grip section 130 once they are assembled together.

Figure 11A:
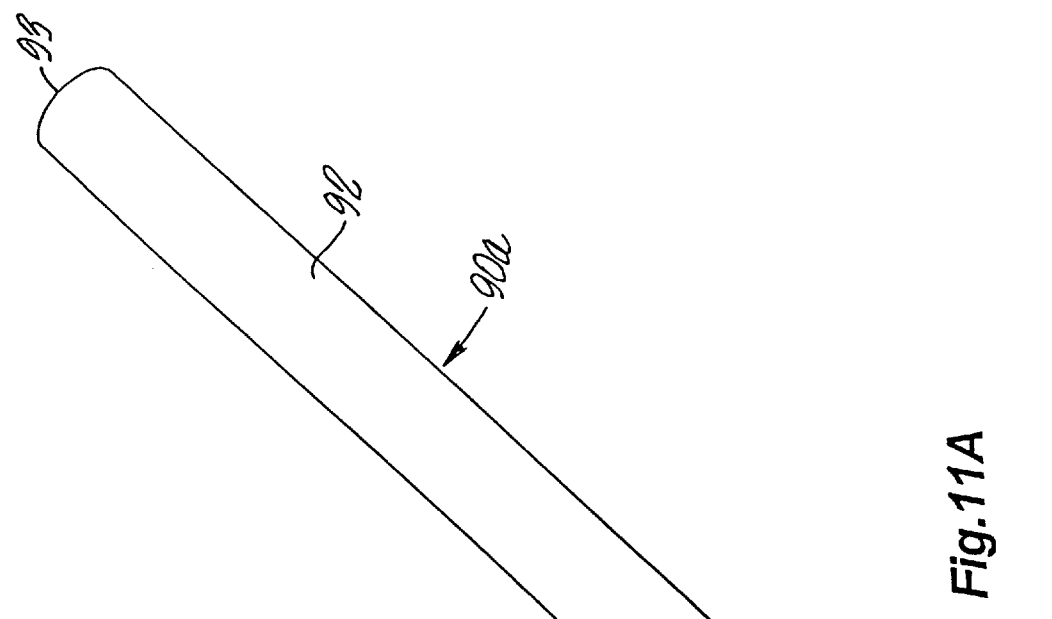
FIGS. 11A and 11B are perspective views of standard unit dose ampules.
Figure 11B:
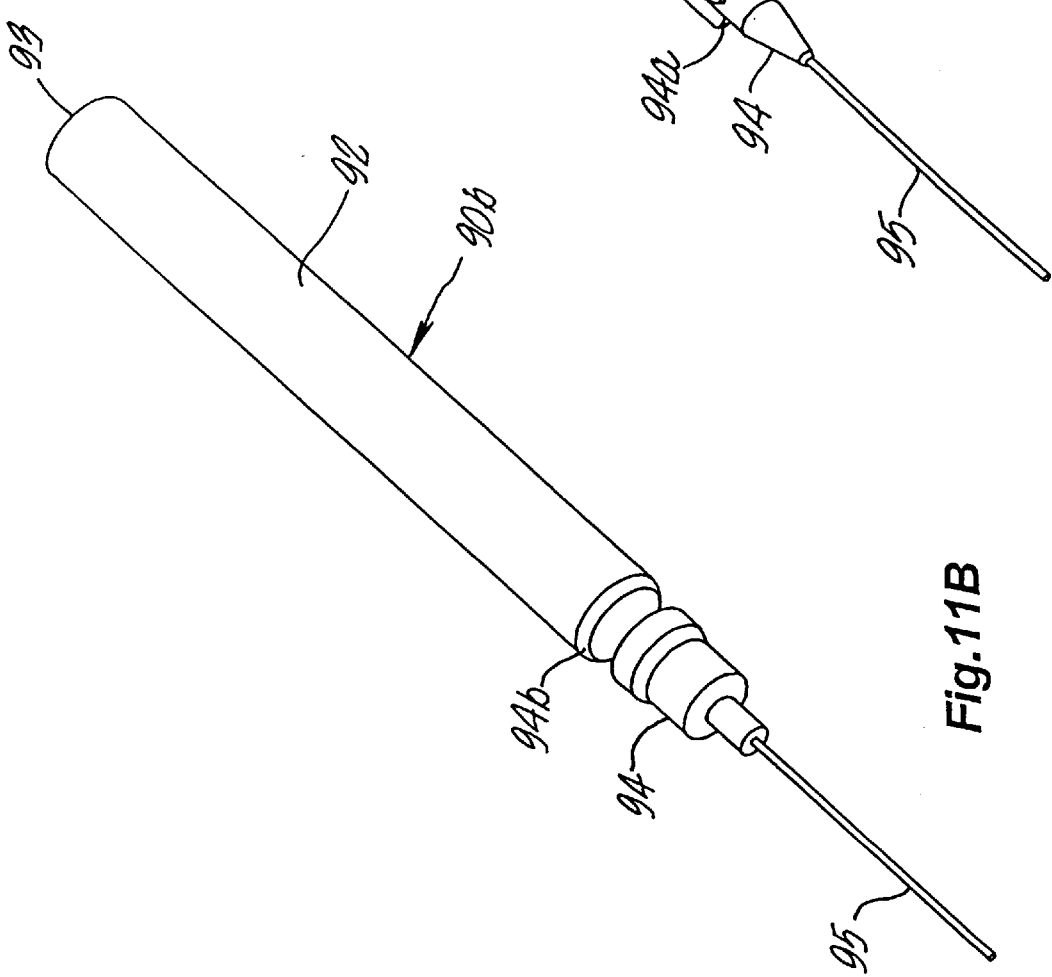

The pre-assembled body 20 and shield 60 and the plunger assembly 120 are then ready to receive a cartridge, such as the conventional unit dose ampules 190a and 190b shown in FIGS. 11A and 11B respectively. The ampules 190 generally comprise a barrel 92, a distal end 94 including a hypodermic needle 95, a needle cover (not shown), and a proximal end 93 having a threaded piston therein (not shown).

Turning again to FIG. 12, the distal end 94 of the ampule 190 is inserted into the open proximal end 22 of the body 20. The ampule 190 enters the cavity 26 and progresses distally until the distal end 94 of the ampule 190 engages the distal end 24 of the body 20. Because different types of distal ends are provided on different ampules, the distal point of engagement between the body 20 and the ampule 190 may vary. For example, a standard Carpuject ampule 190a, shown in FIG. 11A, requires the body 20 to have a distal end 24 similar to that shown in FIG. 8C, such that the distal ribs 94a on the ampule 190a enter the opening 34 in the distal end 24 of the body 20. In contrast, a standard Tubex ampule 190b, shown in FIG. 11B, requires a distal end 24 on the body 20 such as the collar 32 shown in FIG. 8B, thereby allowing the edge 94b on the ampule 190b to engage the collar 32.

Once the ampule 90 is fully inserted into the cavity 26, the plunger assembly 120 is attached to the body 20. The fingers 138 on the finger grip section 130 are aligned with the notches 116 in the finger grip collar 110 on the body 20. The fingers 138 are inserted into the notches 116, compressing the fingers radially as they enter the tapered pockets 118 (FIG. 8D) and pass through the collar 110. Upon reaching the windows 36, the fingers 138 expand radially outward again. The locking detents 139 have blunt proximal edges 139a which engage the distal side of the finger ring 112, thereby substantially permanently locking the plunger assembly 120 to the body 20, and encapsulating the ampule 190 within the cavity 26. When the finger grip section 120 is locked onto the body 20, the distal ends 139b of the fingers 138 preferably engage the proximal end 93 of the ampule 190, preventing proximal movement of the ampule 190. The plunger 122 is attached to the piston (not shown) in the ampule 190, preferably by screwing the threaded bore 127 on the plunger 122 to a threaded nipple (not shown) on the piston.

Referring to FIG. 7, with the shield 60 in the unguarded position, the needle 95 of the ampule 190 extends through the opening 65 and beyond the distal end 63 of the shield 60. The device is then ready to be used to deliver the medication contained within the ampule 190. Similar to the procedure described above, the user places his index and middle fingers on the finger ledges 132, and his thumb in the ring 128. The needle cover (not shown) is removed, the needle 95 is inserted into the patient, and the medication is dispensed by directing the plunger 122 distally with the thumb. As shown in FIG. 7, the windows 64 and 36 allow constant observation of the barrel 92 of the ampule 190, allowing the user to closely monitor delivery of the medication.

Figure 13:
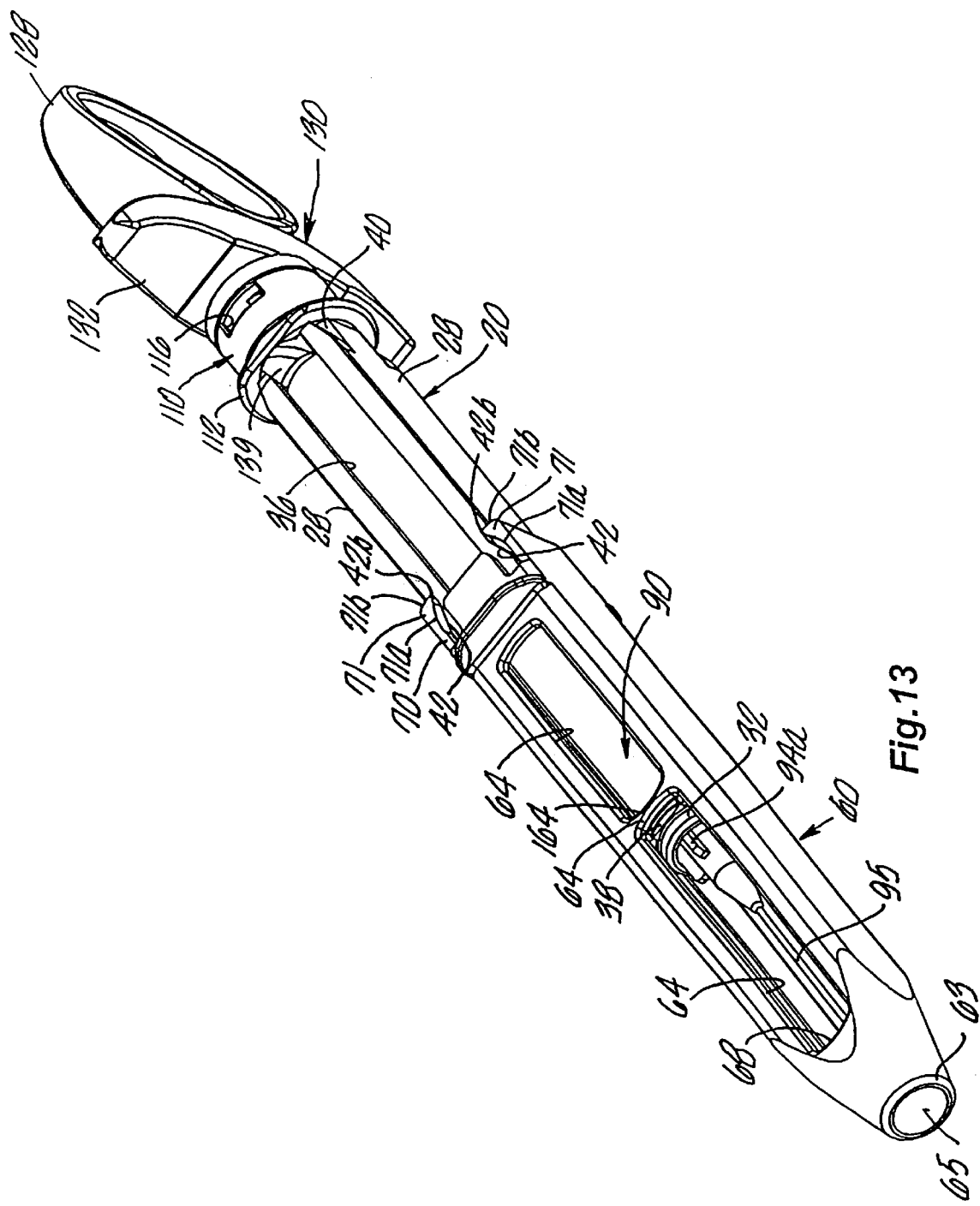
FIG. 13 is a perspective view of the syringe guard holding an ampule, with the shield locked in the guarded position after medication has been dispensed from the ampule.

After the medication is dispensed, the needle 95 is withdrawn from the patient, and the self-shielding feature of the guard 10 is engaged, similar to the procedure described previously. With the fingers of one hand, the body 20 is held while the shield 60 is slid distally into the guarded position, covering the needle 95, as shown in FIG. 13. As the shield 60 is moved distally, the detents 70 leave the proximal detent pockets 40. When the shield reaches the guarded position, the detents 71 enter the distal detent pockets 42, locking the shield 60.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A self-shielding guard for a medical cartridge having a proximal end and a distal end, and having its own needle extending from the distal end, said guard comprising:

a body having a cavity adapted to receive the cartridge axially therein through an open proximal end of said body, and having a distal end including an opening through which the needle may extend when the cartridge is received within said cavity;

locking detents on said proximal end of said body for substantially permanently engaging the proximal end of the cartridge received in said cavity;

a shield slidably attached to said body, and having open proximal and distal ends, said shield being slidable between an unguarded and a guarded position, thereby uncovering and covering respectively the needle on the cartridge; and cooperating detents and detent pockets formed in said body and said shield for mutually engaging to hold said shield in said guarded position;

wherein said cooperating detents and detent pockets comprise:

a first set and a second set of detent pockets formed in said body, said second set being located distally from said first set; and a plurality of detents on said shield adapted to engage said detent pockets, said unguarded position being defined by said detents engaging said first set of detent pockets, and said guarded position being defined by said detents engaging said second set of detent pockets.

2. The self-shielding guard of claim 1 wherein said detents are integrally molded to said shield adjacent said proximal end.

3. The self-shielding guard of claim 1 wherein said detents have sloping distal edges and blunt proximal edges, and wherein said first set of detent pockets have sloping distal edges, whereby said shield may be moved from said unguarded position by slidably disengaging said detents from said first set of detent pockets along said sloping distal edges.

4. The self-shielding guard of claim 1 wherein said second set of detent pockets have blunt proximal edges and said detents have blunt proximal edges, whereby when said shield is directed to said guarded position, said blunt proximal edges of said detents engage said blunt proximal edges of said second set of detent pockets, preventing said shield from being proximally moved from said guarded position.

5. The self-shielding guard of claim 1 wherein said body further comprises a finger grip integrally molded to said proximal end of said body, and wherein said first set of detent pockets are located adjacent said finger grip.

6. A self-shielding guard for a medical cartridge having a proximal end and a distal end, and having its own needle extending from the distal end, said guard comprising:

a body having a cavity adapted to receive the cartridge axially therein through an open proximal end of said body, and having a distal end including an opening through which the needle may extend when the cartridge is received within said cavity;

locking detents on said proximal end of said body for substantially permanently engaging the proximal end of the cartridge received in said cavity;

a shield slidably attached to said body, and having open proximal and distal ends, said shield being slidable between an unguarded and a guarded position, thereby uncovering and covering respectively the needle on the cartridge; and cooperating detents and detent pockets formed in said body and said shield for mutually engaging to hold said shield in said guarded position;

wherein said body further comprises a finger grip section attached to said proximal end of said body, said finger grip section including said locking detents thereon;

wherein said finger grip section comprises a plunger slidably attached to said finger grip section, said plunger having a distal end attachable to a piston in the cartridge, thereby allowing said plunger to slidably direct the piston distally and proximally.

7. A self-shielding guard for a medical cartridge having a proximal end and a distal end, and having its own needle extending from the distal end, said guard comprising:

a body having a cavity adapted to receive the cartridge axially therein through an open proximal end of said body, and having a distal end including an opening through which the needle may extend when the cartridge is received within said cavity;

locking detents on said proximal end of said body for substantially permanently engaging the proximal end of the cartridge received in said cavity;

a shield slidably attached to said body, and having open proximal and distal ends, said shield being slidable between an unguarded and a guarded position, thereby uncovering and covering respectively the needle on the cartridge; and cooperating detents and detent pockets formed in said body and said shield for mutually engaging to hold said shield in said guarded position;

wherein said body further comprises a finger grip section attached to said proximal end of said body, said finger grip section including said locking detents thereon;

wherein said finger grip section includes a plurality of locking fingers, and said proximal end of said body includes tapered pockets adapted to receive said locking fingers, said finger grip section being lockably attached to said body when said locking fingers fully engage said tapered pockets.

* * * * *

UNITED STATES PATENT AND TRADEMARK OFFICE
CERTIFICATE OF CORRECTION

PATENT NO. : 6,171,283 B1
DATED : January 9, 2001
INVENTOR(S) : Perez et al.

It is certified that error appears in the above-identified patent and that said Letters Patent is hereby corrected as shown below:

<u>Title page,</u>
ABSTRACT
Line 5, please change "preassembled" to -- pre-assembled --.

Signed and Sealed this

Twenty-third Day of April, 2002

Attest:

JAMES E. ROGAN
*Attesting Officer*    *Director of the United States Patent and Trademark Office*